United States Patent
Kontani et al.

(10) Patent No.: US 6,903,125 B2
(45) Date of Patent: Jun. 7, 2005

(54) TETRAHYDRO-2H-THIOPYRAN-4-CARBOXAMIDE DERIVATIVE

(75) Inventors: Toru Kontani, Tsukuba (JP); Junji Miyata, Tsukuba (JP); Wataru Hamaguchi, Tsukuba (JP); Tomoaki Kawano, Tsukuba (JP); Akio Kamikawa, Tsukuba (JP); Hiroshi Suzuki, Tsukuba (JP); Kenji Sudo, Tsukuba (JP)

(73) Assignees: Yamanouchi Pharmaceutical Co., Ltd., Tokyo (JP); Rational Drug Design Laboratories, Tokyo (JP)

( * ) Notice: Subject to any disclaimer, the term of this patent is extended or adjusted under 35 U.S.C. 154(b) by 0 days.

(21) Appl. No.: 10/912,232

(22) Filed: Aug. 6, 2004

(65) Prior Publication Data

US 2005/0032855 A1 Feb. 10, 2005

(30) Foreign Application Priority Data

Aug. 8, 2003 (JP) ..................... P2003-290850

(51) Int. Cl.[7] ....................... A61K 31/41; C07D 271/06
(52) U.S. Cl. ................. 514/364; 514/359; 548/131; 548/100
(58) Field of Search ................. 514/364, 359; 548/131, 100

(56) References Cited

U.S. PATENT DOCUMENTS

| | | | |
|---|---|---|---|
| 6,057,451 A | | 5/2000 | Crute et al. |
| 6,288,091 B1 | * | 9/2001 | Crute et al. ............... 514/346 |
| 6,458,959 B1 | | 10/2002 | Crute et al. |
| 6,500,817 B1 | * | 12/2002 | Fisher et al. ............. 514/210.2 |
| 6,545,055 B1 | | 4/2003 | Zhu et al. |
| 6,638,980 B1 | | 10/2003 | Su et al. |
| 2004/0034232 A1 | | 2/2004 | Kontani et al. |

FOREIGN PATENT DOCUMENTS

| | | |
|---|---|---|
| WO | WO 00/29399 A1 | 5/2000 |
| WO | WO 03/013531 A1 | 2/2003 |
| WO | WO 03/095435 A1 | 11/2003 |

* cited by examiner

Primary Examiner—Deborah C. Lambkin
(74) Attorney, Agent, or Firm—Sughrue Mion, PLLC

(57) ABSTRACT

A pharmaceutical drug, particularly a novel compound useful for the prophylaxis or therapeutic treatment of various diseases involving infections with viruses of the Herpesviridae family, specifically various herpesvirus infections such as varicella (chicken pox) via varicella zoster virus, varicella zoster via recurrent infection with latent varicella zoster virus, herpes labialis and herpes encephalitis via HSV-1 and genital herpes via HSV-2 infection. N-{2-[(4-Substituted phenyl)amino]-2-oxoethyl}tetrahydro-2H-thiopyran-4-carboxamide derivative where the phenyl group is substituted at position 4 with a specific five-membered or 6-membered heteroaryl group, has such great anti-virus activity that the oral dosing thereof at a low dose enabled the therapeutic treatment of the diseases.

9 Claims, No Drawings

US 6,903,125 B2

TETRAHYDRO-2H-THIOPYRAN-4-CARBOXAMIDE DERIVATIVE

FIELD OF THE INVENTION

This invention relates to a pharmaceutical agent, more particularly to a novel tetrahydro-2H-thiopyran-4-carboxamide derivative useful for the prophylaxis and therapeutic treatment of diseases in which herpesvirus is involved.

BACKGROUND OF THE INVENTION

Viruses belonging to the Herpesviridae family cause various infectious diseases in human and animals. For example, it is known that varicella zoster virus (VZV) causes varicella and herpes zoster, and herpes simplex viruses of types 1 and 2 (HSV-1 and HSV-2) cause infections such as herpes labialis and genital herpes, respectively. In recent years, additionally, infectious diseases caused by herpesviruses such as cytomegalovirus (CMV), EB virus (Epstein-Barr virus; EBV), and human herpesviruses 6, 7 and 8 have been elucidated.

Currently, pharmaceutical drugs of nucleic acid series, such as acyclovir (ACV) and its prodrugs varacyclovir (VCV) and fancyclovir (FCV) are used as drugs against herpesviruses, such as VZV and HSV. These pharmaceutical drugs of nucleic acid series are mono-phosphorylated into nucleoside monophosphates by viral thymidine kinase encoded by VZV and HSV and are subsequently converted into triphosphate compounds by cellular enzymes. Finally, the tri-phosphorylated nucleoside analogues are incorporated during the replication of the viral genomes by herpesvirus DNA polymerase, to suppress the extension reaction of the viral DNA chains. Since the reaction mechanism of the existing anti-herpesvirus agents is based on the effect of the "competitive inhibition" toward deoxynucleoside triphosphate, as described above, it is necessary to use these drugs at a high concentration for the exertion of their antiviral effects. In a current state, actually, these anti-herpes drugs of nucleic acid series are clinically administered at a dose as high as several hundreds in mg to several grams per day. Since pharmaceutical drugs of nucleic acid series are readily incorporated into the genome DNA of a host via the host DNA polymerase, further, the mutagenicity thereof draws concerns.

On the other hand, lately, several pharmaceutical drugs of non-nucleic acid series and with anti-herpesvirus activity have been reported. For example, it is disclosed an amide or sulfonamide derivative suppressing the HSV helicase/primase enzyme complex to show anti-HSV-1 activity and anti-CMV activity, as represented by the following formula (G), where the N atom is substituted with thiazolylphenylcarbamoylmethyl group or the like (the pamphlet of the International Publication WO 97/24343). However, the anti-VZV activity of these compounds is not specifically disclosed therein.

(G)

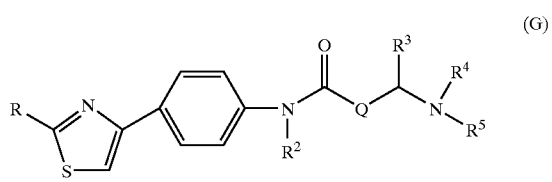

(In the formula, R is hydrogen, a lower alkyl, amino, a lower alkylamino or the like; $R^2$ is hydrogen or a lower alkyl; Q may not exist or when it exists, Q represents methylene; $R^3$ is hydrogen, a lower alkyl or the like; $R^4$ is an unsubstituted or substituted phenyl (lower) alkyl, 1-indanyl, 2-indanyl, (lower cycloalkyl)-(lower alkyl), (Het)-(a lower alkyl) or the like; $R^5$ is phenylsulfonyl, 1- or 2-naphthylsulfonyl, (Het)-sulfonyl, (unsubstituted or substituted phenyl)-Y—$(CH_2)_n$C(O), (Het)-$(CH_2)_n$C(O) or the like wherein Y is O or S and n is 0, 1 or 2; see the Reference 1 for details.)

It is also disclosed an amide or sulfonamide derivative with anti-HSV-1 activity and anti-CMV activity as represented by the following formula (H) wherein the N atom is substituted with thiazolylphenylcarbamoylmethyl group (the pamphlet of the International Publication WO 00/29399). However, the anti-VZV activity of these compounds is not specifically disclosed therein.

(H)

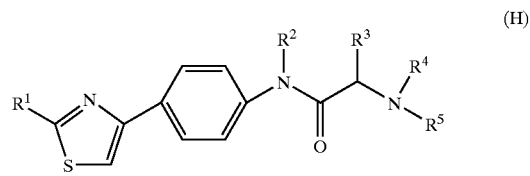

(In the formula, $R^1$ is $NH_2$; $R^2$ is H; $R^3$ is H; $R^4$ is $CH_2Ph$, $CH_2$-(4-pyridyl), $CH_2$-cyclohexyl or the like; and $R^5$ is CO— (substituted phenyl), CO— (unsubstituted or substituted hetero ring) or the like; see the Publication for details.)

The present inventors previously found an amide compound substituted with thiazolylphenylcarbamoylmethyl group and with great anti-VZV activity, as represented by the following formula where the N atom of the amide group is substituted directly with an aromatic group aryl or heteroaryl group, or the salt thereof. Thus, the inventors filed a patent application (the pamphlet of the International Publication WO 02/38554).

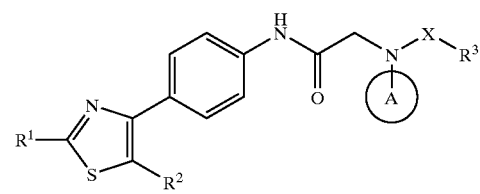

(In the formula, $R^1$ and $R^2$ represent —H, -lower alkyl, —NRaRb, or the like; A represents -aryl which may or may not have a substituent(s) or -heteroaryl which may or may not have a substituent(s) or the like; $R^3$ represents -aryl which may or may not have a substituent(s) or -hetero ring which may or may not have a substituent(s) or the like; X represents CO or $SO_2$; see the Publication for details).

Still now, the creation of an anti-herpesvirus drug with a satisfactory anti-herpesvirus activity and of non-nucleic acid series is strongly desired, which is highly safe at a low dose and suitable for oral dosing.

SUMMARY OF THE INVENTION

The inventors intensively made investigations about a compound with an anti-varicella zoster virus (anti-VZV) action. Consequently, the inventors found that a novel tetrahydro-2H-thiopyran-4-carboxamide derivative as shown by the following general formula (I), where a 1,2,4-oxadiazol-3-yl or 4-oxazolyl group is introduced as Z in the ring structure in place of the amino-substituted thiazole ring in the related art unexpectedly had a great anti-herpesvirus activity. Thus, the invention has been achieved. Compared with the anti-herpesvirus drugs in the related art, the compound of the invention has great pharmacokinetics in biological organisms and shows an excellent anti-virus activity when dosed orally even at a low dose. Additionally, the compound of the invention draws less mutagenic concerns and has a high safety profile, unlike the pharmaceutical drugs of nucleic acid series.

In other words, the invention relates to a novel N-{2-[(4-substituted phenyl)amino]-2-oxoethyl}tetrahydro-2H-thiopyran-4-carboxamide compound represented by the general formula (I).

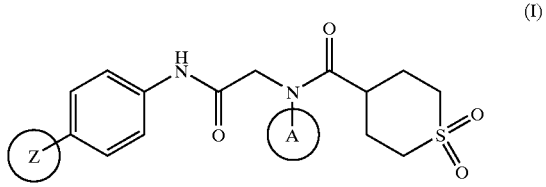

wherein the symbols represent the following meanings:
Z: a 1,2,4-oxadiazol-3-yl or 4-oxazolyl group;
A: a phenyl group substituted with one methyl group, which may or may not have additional one or two substituents selected from the group consisting of a methyl group and halogen atoms, or a 5-indanyl group: the same applies hereinafter.)

The following compounds are preferable, in particular.
(1) The compound with a 1,2,4-oxadiazol-3-yl group as Z.
(2) The compound with a 4-oxazolyl group as Z.
(3) The compound where A is a phenyl group substituted with one methyl group, which may or may not have additional one or two substituents selected from the group consisting of a methyl group and halogen atoms.
(4) The compound with a 5-indanyl group as A.
(5) A compound selected from:
N-(2,6-dimethylphenyl)-N-(2-{[4-(1,3-oxazol-4-yl)phenyl]amino}-2-oxoethyl)tetrahydro-2H-thiopyran-4-carboxamide 1,1-dioxide,
N-(4-methylphenyl)-N-(2-{[4-(1,3-oxazol-4-yl)phenyl]amino}-2-oxoethyl)tetrahydro-2H-thiopyran-4-carboxamide 1,1-dioxide,
N-(3-methylphenyl)-N-(2-{[4-(1,3-oxazol-4-yl)phenyl]amino}-2-oxoethyl)tetrahydro-2H-thiopyran-4-carboxamide 1,1-dioxide,
N-(2-methylphenyl)-N-(2-{[4-(1,3-oxazol-4-yl)phenyl]amino}-2-oxoethyl)tetrahydro-2H-thiopyran-4-carboxamide 1,1-dioxide,
N-(2,4-dimethylphenyl)-N-(2-{[4-(1,3-oxazol-4-yl)phenyl]amino}-2-oxoethyl)tetrahydro-2H-thiopyran-4-carboxamide 1,1-dioxide,
N-(3,4-dimethylphenyl)-N-(2-{[4-(1,3-oxazol-4-yl)phenyl]amino}-2-oxoethyl)tetrahydro-2H-thiopyran-4-carboxamide 1,1-dioxide,
N-(2,3-dihydro-1H-inden-5-yl)-N-(2-{([4-(1,3-oxazol-4-yl)phenyl]amino}-2-oxoethyl)tetrahydro-2H-thiopyran-4-carboxamide 1,1-dioxide,
N-(4-chloro-3-methylphenyl)-N-(2-{[4-(1,3-oxazol-4-yl)phenyl]amino}-2-oxoethyl)tetrahydro-2H-thiopyran-4-carboxamide 1,1-dioxide,
N-(3-fluoro-4-methylphenyl)-N-(2-{[4-(1,3-oxazol-4-yl)phenyl]amino}-2-oxoethyl)tetrahydro-2H-thiopyran-4-carboxamide 1,1-dioxide,
N-(3-fluoro-2,4-dimethylphenyl)-N-(2-{[4-(1,3-oxazol-4-yl)phenyl]amino}-2-oxoethyl)tetrahydro-2H-thiopyran-4-carboxamide 1,1-dioxide,
N-(3,5-difluoro-4-methylphenyl)-N-(2-{[4-(1,3-oxazol-4-yl)phenyl]amino}-2-oxoethyl)tetrahydro-2H-thiopyran-4-carboxamide 1,1-dioxide,
N-(2-fluoro-4-methylphenyl)-N-(2-{[4-(1,3-oxazol-4-yl)phenyl]amino}-2-oxoethyl)tetrahydro-2H-thiopyran-4-carboxamide 1,1-dioxide,
N-(2,3-dimethylphenyl)-N-(2-{[4-(1,2,4-oxadiazol-3-yl)phenyl]amino}-2-oxoethyl)tetrahydro-2H-thiopyran-4-carboxamide 1,1-dioxide,
N-(2,4-dimethylphenyl)-N-(2-{[4-(1,2,4-oxadiazol-3-yl)phenyl]amino}-2-oxoethyl)tetrahydro-2H-thiopyran-4-carboxamide 1,1-dioxide,
N-(2,6-dimethylphenyl)-N-(2-{[4-(1,2,4-oxadiazol-3-yl)phenyl]amino}-2-oxoethyl)tetrahydro-2H-thiopyran-4-carboxamide 1,1-dioxide,
N-(4-fluoro-2,6-dimethylphenyl)-N-(2-{[4-(1,2,4-oxadiazol-3-yl)phenyl]amino}-2-oxoethyl)tetrahydro-2H-thiopyran-4-carboxamide 1,1-dioxide,
N-(2,3-dihydro-1H-inden-5-yl)-N-(2-{[4-(1,2,4-oxadiazol-3-yl)phenyl]amino}-2-oxoethyl)tetrahydro-2H-thiopyran-4-carboxamide 1,1-dioxide,
N-(3-fluoro-4-methylphenyl)-N-(2-{[4-(1,2,4-oxadiazol-3-yl)phenyl]amino}-2-oxoethyl)tetrahydro-2H-thiopyran-4-carboxamide 1,1-dioxide,
N-(4-chloro-3-methylphenyl)-N-(2-{[4-(1,2,4-oxadiazol-3-yl)phenyl]amino}-2-oxoethyl)tetrahydro-2H-thiopyran-4-carboxamide 1,1-dioxide, and
N-(3-fluoro-2,4-dimethylphenyl)-N-(2-{[4-(1,2,4-oxadiazol-3-yl)phenyl]amino}-2-oxoethyl)tetrahydro-2H-thiopyran-4-carboxamide 1,1-dioxide.

Further, the invention relates to a pharmaceutical composition containing the N-{2-[(4-substituted phenyl)amino]-2-oxoethyl}tetrahydro-2H-thiopyran-4-carboxamide compound represented by the general formula (I) and a pharmaceutically acceptable carrier, more specifically to an anti-herpesvirus drug, as well as a therapeutic method for treating diseases in which herpesvirus is involved.

DETAILED DESCRIPTION OF THE INVENTION

The N-{2-[(4-substituted phenyl)amino]-2-oxoethyl}tetrahydro-2H-thiopyran-4-carboxamide compound represented by the general formula (I) in accordance with the invention is further described.

In accordance with the invention, the "halogen atom" includes F, Cl, Br and I atoms.

The compound of the invention encompasses hydrates and various solvates of the N-{2-[(4-substituted phenyl)amino]-2-oxoethyl}tetrahydro-2H-thiopyran-4-carboxamide compound represented by the general formula (I) and polymorphic substances thereof.

Typical methods for producing the compound of the invention are described hereinbelow.

In the following methods, some functional group depending on the type is replaced with an appropriate protective group at the stage of a raw material or intermediate, namely a group readily convertible to the functional group, effectively for the production technique. Afterwards, the protective group is eliminated on a needed basis, to obtain the desired compound. Such functional group includes for example amino group, hydroxyl group, carboxyl group and the like. Such protective group includes for example the protective groups described in Protective Groups in Organic Synthesis, the third edition (T. W. Green and P. G. M. Wuts, eds., JOHN WILLY & SONS, INC.). Depending on the reaction condition, these may appropriately be used. For introducing and eliminating such protective groups, the methods described in the reference can appropriately be applied.

First Method

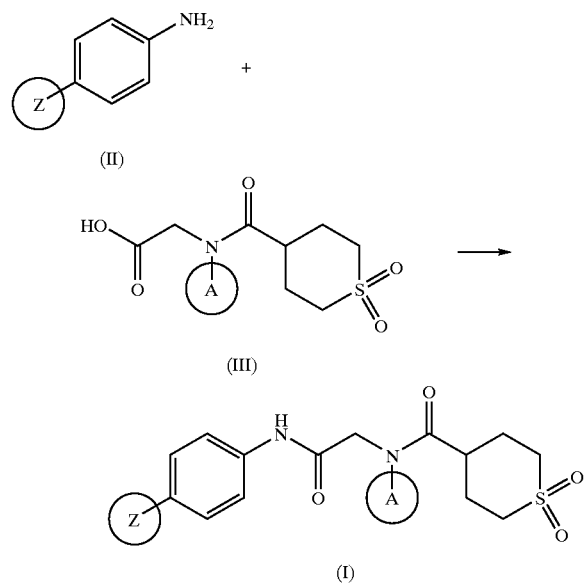

Compound (I) can readily be produced by subjecting the carboxylic acid compound (III) and the aniline derivative (II) to amidation reaction.

The amidation reaction can be done by general methods. For example, the method described in "Courses in Experimental Chemistry" edited by the Chemical Society of Japan, the fourth edition (Maruzen), Vol. 22, p. 137–173 may be applicable. Preferably, the amidation reaction is carried out by converting the carboxylic acid compound (III) to a reactive derivative, for example an acid halide (acid chloride, and the like) or an acid anhydride, and then reacting the resulting reactive derivative with the aniline derivative (II). In case that the reactive derivative of the carboxylic acid is used, preferably, a base [an inorganic base such as sodium hydroxide or an organic base such as triethylamine (TEA), diisopropylethylamine and pyridine] is added.

Additionally, the amidation reaction may be progressed by the reaction of the carboxylic acid in the presence of a condensation agent [1-ethyl-3-(3-dimethylaminopropyl) carbodiimide (WSC), 1,1'-carbonylbis-1H-imidazole (CDI) and the like]. Then, additives such as 1-hydroxybenzotriazole (HOBt) may be added. The reaction temperature can appropriately be selected, depending on the raw material compound. The solvent includes solvents inert to the reaction, for example aromatic hydrocarbon-series solvents such as benzene and toluene, ether-series solvents such as tetrahydrofuran (THF) and 1,4-dioxane, halogenated hydrocarbon-series solvents such as dichloromethane and chloroform, amide-series solvents such as N,N-dimethylformamide (DMF) and N,N-dimethylacetamide, and basic solvents such as pyridine. Depending on the type of the raw material compound and the like, the solvent is appropriately selected. The solvent is used alone or in mixture of two or more types of such solvent.

The individual raw material compounds can readily be produced, using known reactions, for example the reactions described in "Courses in Experimental Chemistry" edited by the Chemical Society of Japan and in the pamphlet of the International Publication WO 02/38554. A typical production method is described hereinbelow.

Production Method of Compound (III)

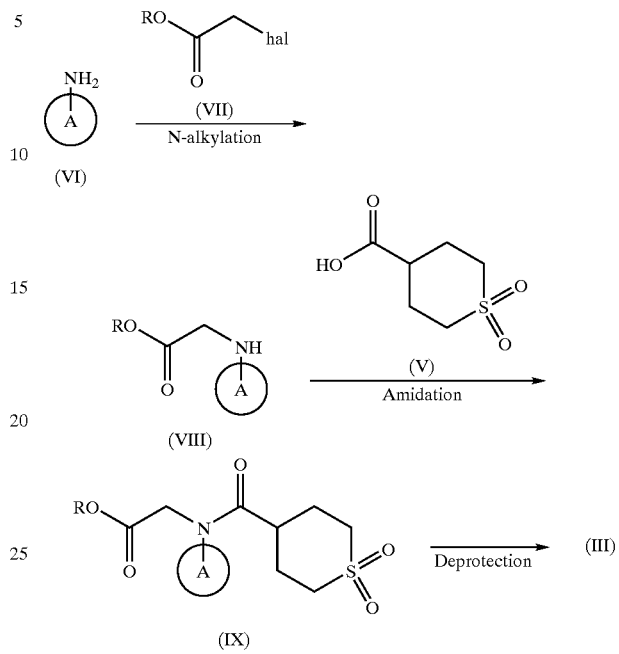

(In the formula, R means a group capable of forming ester residue and includes for example lower alkyl and aralkyl.)

In the reaction scheme above, amidation can progress by the same method as the method described for the first production process.

Using the halogenated alkyl compound (VII), the N-alkylation of the compound (VI) can be done by general methods, for example the method described in the "Courses in Experimental Chemistry" edited by the Chemical Society of Japan, the fourth edition (Maruzen), Vol. 20, p. 279–318. As the reaction temperature, the reaction can be progressed under the temperature of from cooling to heating. The solvent includes solvents inert to the reaction, for example the solvent exemplified for the amidation in the first production method. The reaction is preferably carried out in the presence of a base such as potassium carbonate, sodium hydroxide or sodium hydride. The amidation can be carried out by the same method as the first production method. Herein, the amidation may be first carried out and subsequently, the N-alkylation may be carried out.

The deprotection for obtaining the carboxylic acid compound (III) can be carried out by appropriately applying a general method, depending on the ester type. In case of alkyl esters such as ethyl ester, preferably, the deprotection can be done by treatment with a base such as aqueous sodium hydroxide solution. In case of aralkyl esters such as benzyl ester, the deprotection can be done by reduction in hydrogen atmosphere with palladium-carbon (Pd—C). The reaction can be carried out according to the method described in Protective Groups in Organic Synthesis, the third edition.

A desired raw material compound can be produced by subjecting the compound with some substituent type to a substituent modification reaction well known to a person skilled in the art.

The compound of the invention obtained in this manner is isolated and purified as its free form or as a salt thereof after a salt formation process by a general method. The isolation and purification are carried out by employing general chemical procedures such as extraction, concentration, evaporation, crystallization, filtration, recrystallization, and various chromatographic techniques.

The pharmaceutical composition of the invention which contains one type or two types or more of the compound of the invention can be prepared by methods for general use, using pharmaceutical carriers, excipients and the like for general use in this field. Dosing thereof may satisfactorily be either oral dosing via tablets, pills, capsules, granules, powders, liquids and the like or parenteral dosing via injections via intravenous injections, intramuscular injections and the like, external agents such as ointments, plasters, creams, jellies, paps, sprays, lotions, eye drops, eye ointments and the like, suppositories and inhalation agents.

As the solid composition for oral dosing, tablets, powders, granules and the like are used. In such solid composition, one or more active substances are mixed with at least one inert excipient, for example lactose, mannitol, glucose, hydroxypropyl cellulose, microcrystalline cellulose, starch, polyvinylpyrrolidone, and magnesium metasilicate. According to general methods, the composition may contain inert additives, such as lubricants for example magnesium stearate, disintegrators for example sodium carboxymethyl starch, and dissolution auxiliary agents. On a needed basis, the tablets or pills may satisfactorily be coated with sugar coating or stomach-soluble coating or enteric coating.

The liquid composition for oral dosing includes for example pharmaceutically acceptable emulsions, liquids, suspensions, syrups and elixirs, in which inert solvents for general use, for example distilled water and ethanol can be used. The composition may contain auxiliary agents such as solubilizing agents, moistening agents and suspending agents, sweetening agents, flavoring agents, aromatic agents and preservatives.

The injections for parenteral dosing include for example sterile liquids aqueous or non-aqueous, suspensions and emulsions. The aqueous solvents include for example distilled water for injections and physiological saline. The non-aqueous solvents include for example propylene glycol, polyethylene glycol, vegetable oils such as olive oil, alcohols such as ethanol, and Polysorbate 80 (under trade name). Such composition may contain isotonic agents, preservatives, moistening agents, emulsifying agents, dispersing agents, stabilizers and dissolution auxiliary agents. These are sterilized by filtering through bacteria-retaining filters, blending sterilizing agents, or irradiation. Alternatively, these may be produced into a sterile solid composition and then dissolved or suspended in sterile water or sterile solvents for injections, prior to use.

The external agent includes for example ointments, plasters, creams, jellies, paps, sprays, lotions, eye drops and eye ointments. The external agent contains ointment bases, lotion bases, aqueous and non-aqueous liquids, suspensions, emulsions and the like, for general use. The ointment or lotion bases include for example polyethylene glycol, propylene glycol, white Vaseline, white beeswax, polyoxyethylene hardened castor oil, glycerin monostearate, stearyl alcohol, cetyl alcohol, lauromacrogol, and sorbitan sesquioleate.

Generally, the daily dose of the compound of the invention is about 0.001 to 50 mg/kg/body weight, preferably 0.01 to 30 mg/kg/body weight, more preferably 0.05 to 10 mg/kg/body weight for oral dosing and the daily dose is about 0.0001 to 10 mg/kg/body weight, preferably 0.001 to 1.0 mg/kg/body weight for intravenous dosing. The dose is administered once or in dividend portions daily. The dose is appropriately determined, depending on each case, in terms of the symptom, age, sex and the like. In case that the compound of the invention is to be used as an external agent, an external agent containing the compound of the invention at 0.0001 to 20%, preferably 0.01 to 10%. The external agent is administered locally once or in dividend portions daily, depending on the symptom.

The compound of the invention may appropriately be used in combination with other pharmaceutical agents. The pharmaceutical agents usable in combination include for example other anti-herpesvirus agents such as ACV, VCV, FCV, pencyclovir (PCV), vidarabine (ara-A), BVDU (bromovinyldeoxyuridine), foscarnet (PFA), and gancyclovir (GCV); analgesics for neuralgia after varicella zoster, such as amitriptyline (tricyclic anti-depression agent), gabapentin (anti-spasm agent), lidocaine and mexiletine (anti-arrhythmia agent), and capsicin; and antiphlogistic analgesics such as indometacin, ibuprofen, and celecoxib.

The effects of the compound of the invention were confirmed at the following pharmacological tests.

TEST EXAMPLE 1

Anti-VZV Activity Assay

This experiment was carried out based on the method described by Shigeta S., The Journal of Infectious Diseases, 147, 3, 576–584 (1983). Briefly, 10,000 human embryonic fibroblast (HEF) cells were inoculated in a 96-well microtiter plate, using a growth culture medium [Eagle MEM (Nissui) supplemented with 10% (v/v) fetal bovine serum (FBS; Sigma)], for culturing in 5% $CO_2$ at 37° C. for 4 days until a monolayer was formed. After the cells were washed with a maintenance culture medium (MEM supplemented with 2% FBS), VZV (strain CaQu) preliminarily diluted to 20 to 30 pfu/100 $\mu$l with the maintenance culture medium was inoculated at 100 $\mu$l/well. The plate was centrifuged at 2,000 rpm at ambient temperature for 20 minutes and was then incubated in 5% $CO_2$ at 37° C. for 3 hours, for infection with VZV. After the plate was washed three times with the maintenance culture medium, 100 $\mu$l of a test drug diluted to an appropriate concentration with the maintenance culture medium was added to each well. After the cells were cultured in 5% $CO_2$ at 37° C. for 3 to 4 days, 10% formalin/PBS was added at 100 $\mu$l/well to fix the cells for 2 to 3 hours. After discarding the fixing solution and culture supernatant and subsequently washing the plate with water, a staining solution (0.025% Crystal Violet) was added at 50 $\mu$l/well for staining for 2 to 3 minutes, and then, the plate was washed with water and dried at 37° C. Cellular death is induced in the HEF cells infected with VZV, so that plaques of the dead cells are formed in the monolayer of the HEF cells. The number of such plaques was counted with a microscope, to calculate the $EC_{50}$ value of the test drug as a concentration to inhibit 50% of the plaques.

Compared with acyclovir with the $EC_{50}$ value of 3.4 $\mu$M, the $EC_{50}$ values of Examples 1, 11, 13, 27, 37 and 39 of the invention are 0.075, 0.060, 0.033, 0.10, 0.095 and 0.082 $\mu$M in this order. It was verified that the compounds of the Examples had great anti-VZV activity.

TEST EXAMPLE 2

Anti-HSV-1 Activity Assay 10,000 MRC-5 cells were inoculated and cultured in a 96-well microtiter plate, using the growth culture medium in 5% $CO_2$ at 37° C. for 4 to 5 days until a monolayer was formed. After the cells were washed with the maintenance culture medium, 100 μl of the maintenance culture medium dissolving therein an appropriate concentration of a test reagent was added to each well. Immediately after the test drug was added, an HSV-1 (strain KOS) solution was inoculated at 50 $TCID_{50}$ (50% tissue culture infectious dose)/100 μl.

After the cells were cultured in 5% $CO_2$ at 37° C. for 5 days, 20 μl of MTT solution [3-(4,5-dimethyl-2-thiazolyl)-2,5-diphenyl-2H-tetrazolium bromide; Sigma] (diluted with PBS to 7.5 mg/ml) was added to each well, for another 24-hour incubation. After the culture medium was discarded, 100 μl of a solvent (prepared by adding 10% (v/v) Triton X 100 and 0.4% hydrochloric acid to isopropanol) was added to each well, to solubilize the generated formazan. The absorbance at 540 nm or 690 nm was measured with a microplate reader. Based on the suppression ratio (%) of the cellular death of the MRC-5 cell via HSV-1 replication, the $EC_{50}$ value of the test drug was calculated.

Compared with acyclovir with the $EC_{50}$ value of 0.48 μM, the $EC_{50}$ values of the compounds of Examples 1, 11, 13, 27, 37 and 39 of the invention are 0.075, 0.040, 0.0060, 0.060, 0.026, and 0.029 μM in this order. It was verified that the compounds of the Examples had great anti-HSV activity.

TEST EXAMPLE 3
Cutaneously HSV-1-Infected Hairless Mice Model

Female hairless mice [HR-1, 7 weeks of age] were infected with a virus suspension containing HSV-1 strain WT-51 ($1.5 \times 10^4$ PFU/15 μl) on the lateral side of the body, which had scratched with a needle, while anesthetized with diethyl ether, as previously described by H. Machida et al. [Antiviral Res., 1992, 17, 133–143]. Tested compounds were administered orally as a methyl cellulose suspension, except for compounds marked with asterisk which were dissolved in 20% Cremophor EL and 20% polyethylene glycol, starting at 3 hours after the infection, and then at a dose of 10 mg/kg twice daily for a period of 5 days. Hairless mice were inspected daily and disease severity was determined using the following criteria:

Score 0: no signs of infection.
Score 1: localized, barely perceptible small vesicles.
Score 2: slight vesicle spread.
Score 3: large patches of vesicles formed.
Score 4: zosteriform vesicles.
Score 5: large patches of ulcers formed.
Score 6: zosteriform with severe large ulcers.
Score 7: hind limb paralysis or death.

The zosteriform skin lesion and neurological scores for each animal were combined to produce a composite score. The mean composite score was used to represent the disease in each study group. The disease course was measured for 17 days and the extent of the disease was represented by the area under the curve (AUC) of the mean daily composite disease score each day after viral inoculation. The inhibitory activities of tested compounds were calculated using the AUCs.

Table 1

TABLE 1

| Test compound | Inhibitory activity (%) | Test compound | Inhibitory activity (%) |
|---|---|---|---|
| Example 1 | *93 | Example 19 | 71 |
| Example 2 | 85 | Example 20 | 91 |
| Example 3 | 70 | Example 24 | 69 |
| Example 4 | 77 | Example 25 | *70 |
| Example 6 | 92 | Example 27 | 86 |
| Example 8 | 91 | Example 31 | *86 |
| Example 11 | 92 | Example 33 | 79 |
| Example 13 | 89 | Example 35 | 82 |
| Example 14 | 98 | Example 37 | 100 |
| Example 17 | 94 | Example 39 | 80 |
| Comparative Compound A | 38 | Comparative Compound B | 2 |
| Comparative Compound C | 44 | Comparative Compound D | 43 |

Comparative Compound A:

Compound of Example 49, Reference 3

Comparative Compound B:

Compound of Example 85, Reference 3

Comparative Compound C:

Compound of Example 87, Reference 3

Comparative Compound D:
Compound of Example 119, Reference 3

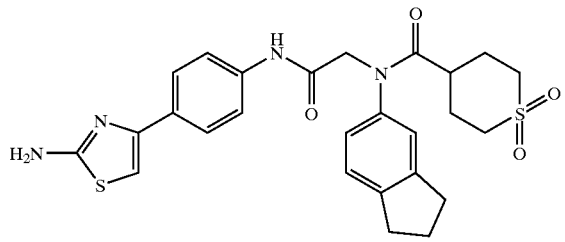

The inhibition ratio of the lesions in the groups administered with the compound of the invention was as high as 70 to 100%, which verifies that the compound of the invention has greater suppressive activity of the exacerbation of the lesions than the representative compound tested herein, disclosed in Reference 3.

It was expected that the compound of the invention would possibly be more highly safe anti-herpesvirus agent, because the compound never belongs to nucleic acid series and actually exerted great anti-virus activity at a low dose.

Additionally, the compound of the invention has weaker inhibitory activity against CYP enzymes than the that of the compounds disclosed in Reference 3. This property of the compound of the invention is therefore advantageously useful in clinical situation with little concern about drug—drug interaction with other drugs.

Production examples of the compound of the invention are shown below in Examples. Herein, many of the raw material compounds for use in the following reactions are known in Reference 3 (the pamphlet of the International Publication WO 02/38554) and the like, and can therefore be readily available according to the methods described in these known references. Production examples of novel compounds among the raw materials are shown below in Reference Examples.

REFERENCE EXAMPLE 1

5% Palladium-carbon powder was added to a suspension of 4-(4-nitrophenyl)-1,3-oxazole in mixture of ethanol and tetrahydrofuran, and the reaction mixture was stirred under 1 atm of hydrogen at ambient temperature for 12 hours. The reaction mixture was filtered through Celite, and the resulting filtrate was concentrated under reduced pressure. The resulting crude product was purified by silica gel column chromatography, to obtain [4-(1,3-oxazol-4-yl)phenyl]amine (pale yellow solid). Electron Impact-MS (M)+:160.

REFERENCE EXAMPLE 2

Potassium carbonate and ethyl bromoacetate were added to a DMF solution of 4-methylaniline. The resulting mixture was stirred under heating. After water and ethyl acetate were added to the reaction mixture, the organic layer was separated, and rinsed and dried, from which the solvent was distilled off under reduced pressure to obtain a crude product. The crude product was dissolved in methylene chloride, to which pyridine and tetrahydro-2H-thiopyran-4-carbonyl chloride 1,1-dioxide were added under stirring. After the reaction solution was concentrated, 1M hydrochloric acid and chloroform were added to the resulting residue. The organic layer was separated, rinsed and dried, from which the solvent was distilled off under reduced pressure. The resulting crude product was purified by silica gel column chromatography, to obtain ethyl {[(1,1-dioxotetrahydro-2H-thiopyran-4-yl)carbonyl](4-methylphenyl)amino}acetate (colorless oily matter). FAB-MS [(M+H)+]: 354.

REFERENCE EXAMPLES 3 THROUGH 15

Compounds of Reference Examples 3 through 15 as shown below in Table 2 were obtained by the same treatment as in Reference Example 2.

EXAMPLE 1

To an ethanol (10 ml) solution of ethyl {(2,6-dimethylphenyl)[(1,1-dioxide tetrahydro-2H-thiopyran-4-yl)carbonyl]amino}acetate (735 mg) was added aqueous 1M sodium hydroxide solution (2.3 mL), for stirring at ambient temperature for 5 hours. After 1M hydrochloric acid was added to the reaction mixture to prepare the solution into acidity, water and chloroform were added thereto to separate the organic layer. Further, the organic layer was dried over anhydrous sodium sulfate and filtered, and then, the solvent was distilled off under reduced pressure. After the resulting crude carboxylic acid product was dissolved in chloroform (15 ml), WSC.HCl (422 mg) and [4-(1,3-oxazol-4-yl)phenyl]amine (320 mg) were added sequentially to the resulting solution, for stirring at ambient temperature for 4 hours. After saturated sodium hydrogen carbonate solution and chloroform were added to the reaction solution, the organic layer was separated. The organic layer was rinsed in saturated sodium chloride solution, dried over anhydrous magnesium sulfate and filtered, from which the solvent was distilled off under reduced pressure. The resulting crude product was rinsed in hexane-ethyl acetate (=3/2), and then recrystallized in ethanol, to obtain N-(2,6-dimethylphenyl)-N-(2-{[4-(1,3-oxazol-4-yl)phenyl]amino}-2-oxoethyl)tetrahydro-2H-thiopyran-4-carboxamide 1,1-dioxide (colorless crystal) at 610 mg.

EXAMPLES 2 THROUGH 40

Compounds of Examples 2 through 40 shown below in Tables 3 through 9 were obtained by the same treatment as in Example 1.

The physicochemical properties of the compounds of the Reference Examples are shown in Table 2, while Table 3 shows the structures and physicochemical properties of the compounds of the Examples.

Abbreviations in the tables individually have the following meanings. Ref: Reference Example; Ex: Example; Dat: physico-chemical properties {F+: FAB-MS [(M+H)+]; F−: FAB-MS [(M−H)−]{; EI: Electron Impact-MS (M)+; ESI+: ESI (electrospray ionization)-MS [(M+H)+]; N1: the characteristic peak δ ppm of $^1$H-NMR (DMSO-d$_6$, TMS internal standard); Ph: phenyl; and Me: methyl. Herein, the numerical figure before each substituent group indicates the position for its substitution. For example, 3,4-Cl$_2$-5-F—Ph indicates 3,4-dichloro-5-fluorophenyl group.

INDUSTRIAL APPLICABILITY

The compound of the invention has great anti-herpesvirus action and exerts great anti-virus action even at a low dose of oral dosing, compared with anti-herpes agents in the related art. Thus, the compound of the invention is useful for the prophylaxis or therapeutic treatment of various herpesvirus infections such as varicella (chicken pox) via VZV infection, varicella zoster via recurrent infection with latent VZV, herpes labialis and herpes encephalitis via HSV-1 infection and genital herpes via HSV-2 infection, as a pharmaceutical drug, particularly as a highly safe anti-herpesvirus agent.

TABLE 2

(III)

[Structure: RO-CH2-C(=O)-N(A)-C(=O)-tetrahydrothiopyran-1,1-dioxide]

| Ref | A | R | Dat | Ref | A | R | Dat |
|---|---|---|---|---|---|---|---|
| 3 | 2,3-(Me)₂—Ph | Et | F+: 368 | 4 | 4-Me—Ph | Et | F+: 354 |
| 5 | 2,5-(Me)₂—Ph | Et | F+: 368 | 6 | 3-Me—Ph | Et | F+: 354 |
| 7 | 3,4-(Me)₂—Ph | Et | F+: 368 | 8 | 2-Me—Ph | Et | F+: 354 |
| 9 | 2,4,6-(Me)₃—Ph | Et | F+: 382 | 10 | 2,4-(Me)₂—Ph | Et | F+: 368 |
| 11 | 4-F-3-Me—Ph | Et | F+: 372 | 12 | 2,6-(Me)₂—Ph | Et | F+: 368 |
| 13 | 3-Br-4-Me—Ph | Et | F+: 432, 434 | 14 | 4-F-2,6-(Me)₂—Ph | Et | F+: 386 |
| 15 | 3,5-(Me)₂—Ph | Et | F+: 368 | | | | |

TABLE 3

(Ia)

[Structure: oxazolyl-phenyl-NH-C(=O)-CH2-N(A)-C(=O)-tetrahydrothiopyran-1,1-dioxide]

| Ex | A | Dat | | |
|---|---|---|---|---|
| 1 | 2,6-(Me)₂—Ph | F+: | 482 | |
| | | N1: | 1.87–2.42(5H, m), 2.13(6H×0.1, s), 2.33 (6H×0.9, s), 2.97–3.27(4H, m), 4.19(2H× 0.9, s), 4.48(2H×0.1, s), 7.07–7.25(3H, m), 7.62–7.66(2H, m), 7.72–7.75(2H, m), 8.43 (1H, d), 8.54(1H, d), 10.15(1H, brs) | |
| 2 | 4-Me—Ph | F+: | 468 | |
| | | N1: | 1.98–2.06(4H, m), 2.34(3H, s), 2.68–2.70 (1H, m), 2.97–3.02(4H, m), 4.35(2H, s), 7.28(2H, d), 7.36(2H, d), 7.63–7.66(2H, m), 7.72–7.76(2H, m), 8.43(1H, s), 8.54(1H, s), 10.14(1H, s) | |
| 3 | 3-Me—Ph | F+: | 468 | |
| | | N1: | 2.01–2.09(4H, m), 2.35(3H, s), 2.71(1H, m), 2.93–3.06(4H, m), 4.36(2H, s), 7.17–7.38 (4H, m), 7.64(2H, d), 7.73(2H, d), 8.43(1H, d), 8.54(1H, d), 10.15(1H, s) | |
| 4 | 2-Me—Ph | F+: | 468 | |
| | | N1: | 1.88–2.15(4H, m), 2.15(3H×0.1, s), 2.26 (3H×0.9, s), 2.41–2.46(1H, m), 2.83–3.05 (4H, m), 3.86(1H×0.9, d), 4.20(1H×0.1, d), 4.74(1H×0.9, d), 4.84(1H×0.1, d), 7.09–7.77(8H, m), 8.43(1H, d), 8.53(1H, d), 10.14 (1H×0.9, s), 10.19(1H×0.1, s) | |
| 5 | 2,3-(Me)₂—Ph | F+: | 482 | |
| | | N1: | 1.85–2.12(4H, m), 2.03(3H×0.1, s), 2.15 (3H×0.9, s), 2.25(3H×0.1, s), 2.31(3H×0.9, s), 2.42–2.47(1H, m), 2.83–2.90(1H, m), 3.00–3.22(3H, m), 3.84(1H×0.9, d), 4.16 (1H×0.1, d), 4.72(1H×0.9, d), 4.84(1H×0.1, d), 7.07–7.36(3H, m), 7.62–7.66(2H, m), 7.71–7.76(2H, m), 8.43(1H, brs), 8.54(1H, d), 10.12(1H×0.9, s), 10.16(1H×0.1, s) | |

TABLE 4

| Ex | A | Dat | |
|---|---|---|---|
| 6 | 2,4-(Me)₂—Ph | F+: | 482 |
| | | N1: | 1.88–2.50(5H, m), 2.09(3H×0.1, s), 2.21 (3H×0.9, s), 2.25(3H×0.1, s), 2.30(3H× 0.9, s), 2.85–3.20(4H, m), 3.81(1H×0.9, d), 4.17(1H×0.1, d), 4.72(1H×0.9, d), 4.81(1H×0.1, d), 6.97–7.39(3H, m), 7.62–7.66(2H, m), 7.72–7.76(2H, m), 8.43(1H, s), 8.54(1H, s), 10.11(1H×0.9, s), 10.17(1H×0.1, s) |
| 7 | 2,5-(Me)₂—Ph | F+: | 482 |
| | | N1: | 1.86–2.51(5H, m), 2.08(3H×0.1, s), 2.20 (3H×0.9, s), 2.22(3H×0.1, s), 2.30(3H× 0.9, s), 2.87–3.26(4H, m), 3.84(1H×0.9, d), 4.21(1H×0.1, d), 4.70(1H×0.9, d), 4.80(1H×0.1, d), 6.92–7.32(3H, m), 7.63–7.65(2H, m), 7.72–7.76(2H, m), 8.43(1H, s), 8.54(1H, s), 10.12(1H×0.9, s), 10.17 (1H×0.1, s) |
| 8 | 3,4-(Me)₂—Ph | F+: | 482 |
| | | N1: | 1.92–2.08(4H, m), 2.09(3H, s), 2.24(3H, s), 2.71(1H, m), 2.94–3.06(4H, m), 4.33 (2H, S), 7.17–7.24(3H, m), 7.64(2H, d), 7.73(2H, d), 8.43(1H, s), 8.54(1H, s), 10.12(1H, s) |
| 9 | 3,5-(Me)₂—Ph | F+: | 482 |
| | | N1: | 1.96–2.14(4H, m), 2.30(6H, s), 2.73(1H, m), 2.95–3.04(4H, m), 4.33(2H, S), 7.02 (1H, s), 7.08(2H, s), 7.64(2H, d), 7.73 (2H, d), 8.43(1H, s), 8.54(1H, s), 10.12 (1H, s) |
| 10 | 2,4,6-(Me)₃—Ph | F+: | 496 |
| | | N1: | 1.87–2.45(5H, m), 2.08(3H×0.1, s), 2.09 (6H×0.1, s), 2.27(3H×0.9, s), 2.28(6H× 0.9, s), 3.01–3.26(4H, m), 4.16(2H×0.9, s), 4.44(2H×0.1, s), 6.88(2H×0.1, s), 7.01 (2H×0.9, s), 7.61–7.65(2H, m), 7.71–7.75 (2H, m), 8.43(1H, s), 8.54(1H, s), 10.12 (1H×0.9, s), 10.14(1H×0.1, s) |
| 11 | 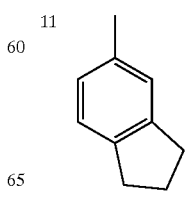 | F+: | 494 |
| | | N1: | 2.01–2.08(6H, m), 2.70–3.06(9H, m), 4.34(2H, s), 7.13–7.32(3H, m), 7.64(2H, d), 7.73(2H, d), 8.43(1H, s), 8.54(1H, s), 10.13(1H, s) |

TABLE 5

| | | |
|---|---|---|
| 12 | 3-Cl-4-Me—Ph | F+: 502<br>N1: 2.01–2.06(4H, m), 2.36(3H, s), 2.68–2.75(1H, m), 3.01–3.06(4H, m), 4.37(2H, S), 7.37–7.40(1H, m), 7.46(2H, d), 7.60–7.66(3H, m), 7.74(2H, d), 8.44(1H, s), 8.55(1H, s), 10.18(1H, s) |
| 13 | 4-Cl-3-Me-Ph | F+: 502<br>N1: 2.00–2.06(4H, m), 2.36(3H, s), 2.68–2.75(1H, m), 3.01–3.04(4H, m), 4.36(2H, S), 7.33–7.36(1H, m), 7.48–7.52(2H, m), 7.64(2H, d), 7.73(2H, d), 8.43(1H, s), 8.54(1H, s), 10.18(1H, s) |
| 14 | 3-F-4-Me-Ph | F+: 486<br>N1: 2.00–2.05(4H, m), 2.26(3H, s), 2.70–2.77(1H, m), 3.01–3.03(4H, m), 4.36(2H, S), 7.24–7.26(1H, m), 7.32–7.41(2H, m), 7.64(2H, d), 7.73(2H, d), 8.43(1H, s), 8.54(1H, s), 10.17(1H, s) |
| 15 | 3-Br-4-Me—Ph | F+: 546, 548<br>N1: 2.00–2.06(4H, m), 2.38(3H, s), 2.68–2.74(1H, m), 3.01–3.04(4H, m), 4.36(2H, S), 7.41–7.47(2H, m), 7.64(2H, d), 7.73–7.76(3H, m), 8.43(1H, s), 8.54(1H, s), 10.18(1H, s) |
| 16 | 5-F-2-Me-Ph | F+: 486<br>N1: 1.88–2.15(4H, m), 2.11(3H×0.1, s), 2.23(3H×0.9, s), 2.45–2.49(1H, m), 2.96–3.16(4H, m), 3.92(1H×0.9, d), 4.27(1H×0.1, d), 4.70(1H×0.9, d), 4.82(1H×0.1, d), 6.95–6.98(1H×0.1, m), 7.06–7.10(1H×0.1, m), 7.20–7.25(1H×0.9, m), 7.29–7.33(1H×0.1, m), 7.37–7.7.40(1H×0.9, m), 7.42–7.46(1H×0.1, m), 7.65(2H, d), 7.74(2H, d), 8.43(1H, s), 8.54(1H, s), 10.18(1H×0.9, s), 10.23(1H×0.1, s) |
| 17 | 3-F-2,4-(Me)₂-Ph | F+: 500<br>N1: 1.88–2.23(4H, m), 2.03(3H×0.1, s), 2.16(3H×0.9, s), 2.20(3H×0.1, s), 2.26(3H×0.9, s), 2.47–2.54(1H, m), 2.87–3.17(4H, m), 3.91(1H×0.9, d), 4.25(1H×0.1, d), 4.66(1H×0.9, d), 4.80(1H×0.1, d), 6.88 (1H×0.1, d), 7.10(1H×0.1, dd), 7.21 (1H×0.9, dd), 7.28(1H×0.9, d), 7.64(2H, d), 7.73(2H, s), 8.43(1H, s), 8.54(1H, s), 10.14(1H×0.9, s), 10.20(1H×0.1, s) |

TABLE 6

| | | |
|---|---|---|
| 18 | 4-F-3,5-(Me)₂-Ph | F+: 500<br>N1: 2.00–2.05(4H, m), 2.24(6H, s), 2.67–2.74(1H, m), 3.00–3.04(4H, m), 4.33(2H, S), 7.23(2H, d), 7.65 (2H, d), 7.74(2H, d), 8.43(1H, s), 8.54(1H, s), 10.15(1H, s) |
| 19 | 3,5-F₂-4-Me-Ph | F+: 504<br>N1: 1.99–2.05(4H, m), 2.17(3H, s), 2.75–2.82(1H, m), 2.99–3.10(4H, m), 4.37(2H, S), 7.28(2H, d), 7.65 (2H, d), 7.74(2H, d), 8.44(1H, s), 8.55(1H, s), 10.21(1H, s) |
| 20 | 2-F-4-Me-Ph | F+: 486<br>N1: 1.89–2.11(4H, m), 2.30(3H×0.1, s), 2.36(3H×0.9, s), 2.60–2.68(1H, m), 3.01–3.26(4H, m), 3.94(1H×0.9, d), 4.02(1H×0.1, d), 4.50(1H×0.1, d), 4.76(1H×0.9, d), 7.00(1H×0.1, d), 7.09(1H×0.1, m), 7.12(1H×0.9, d), 7.24(1H×0.9, d), 7.38 (1H×0.1, dd), 7.50(1H×0.9, dd), 7.63(2H, d), 7.73(2H, d), 8.44(1H, s), 8.55(1H, s), 10.17(1H×0.9, s), 10.23(1H×0.1, s) |

TABLE 7

(Ib)

[Structure shown]

| Ex | A | | Dat |
|---|---|---|---|
| 21 | 4-Me—Ph | F+: | 469 |
| | | N1: | 1.94–2.11(4H, m), 2.34(3H, s), 2.65–2.75 (1H, m), 2.92–3.08(4H, m), 4.38(2H, s), 7.28(2H, d), 7.37(2H, d), 7.79(2H, d), 8.00 (2H, d), 9.66(1H, s), 10.38(1H, s) |
| 22 | 3-Me—Ph | F−: | 467 |
| | | N1: | 1.96–2.11(4H, m), 2.35(3H, s), 2.65–2.76 (1H, m), 2.92–3.09(4H, m), 4.39(2H, s), 7.20–7.39(4H, m), 7.79(2H, d), 8.00(2H, d), 9.66(1H, s), 10.38(1H, s) |
| 23 | 2-Me—Ph | F+: | 469 |
| | | N1: | 1.88–2.26(4H+3H, m), 2.42–2.52(1H, m), 2.84–3.18(4H, m), 3.91(1H×0.9, d), 4.44 (1H×0.1, d), 4.75(1H×0.9, d), 4.87(1H×0.1, d), 7.08–7.54(4H, m), 7.75–7.81(2H, m), 7.97–8.04(2H, m), 9.66(1H×0.9, s), 9.67 (1H×0.1, s), 10.37(1H×0.9, s), 10.41(1H× 0.1, s) |
| 24 | 2,3-(Me)₂—Ph | F−: | 481 |
| | | N1: | 1.83–2.31(4H+3H+3H, m), 2.42–2.54(1H, m), 2.82–3.16(4H, m), 3.88(1H×0.9, d), 4.19 (1H×0.1, d), 4.72(1H×0.9, d), 4.87(1H×0.1, d), 7.05–7.37(3H, m), 7.75–7.80(2H, m), 7.97–8.03(2H, m), 9.66(1H×0.9, s), 9.66 (1H×0.1, s), 10.35(1H×0.9, s), 10.38 (1H×0.1, s) |
| 25 | 2,4-(Me)₂—Ph | F−: | 481 |
| | | N1: | 1.84–2.33(4H+3H+3H, m), 2.42–2.52(1H, m), 2.84–3.19(4H, m), 3.86(1H×0.9, d), 4.21 (1H×0.1, d), 4.73(1H×0.9, d), 4.84(1H×0.1, d), 6.95–7.40(3H, m), 7.75–7.81(2H, m), 7.98–8.02(2H, m), 9.66(1H×0.9, s), 9.66 (1H×0.1, s), 10.35(1H×0.9, s), 10.39(1H× 0.1, s) |

TABLE 8

| Ex | A | | Dat |
|---|---|---|---|
| 26 | 2,5-(Me)₂—Ph | F−: | 481 |
| | | N1: | 1.84–2.32(4H+3H+3H, m), 2.42–2.52(1H, m), 2.87–3.18(4H, m), 3.89(1H×0.9, d), 4.25(1H×0.1, d), 4.72(1H×0.9, d), 4.83(1H×0.1, d), 6.92–7.34(3H, m), 7.76–7.82 (2H, m), 7.98–8.04(2H, m), 9.66 (1H×0.9, s), 9.67(1H×0.1, s), 10.37(1H×0.9, s), 10.39(1H×0.1, s) |
| 27 | 2,6-(Me)₂—Ph | F−: | 481 |
| | | N1: | 1.88–2.42(5H+6H, m), 2.98–3.27 (4H, m), 4.22(2H×0.86, s), 4.51 (2H×0.14, s), 7.1–7.3(3H, m), 7.76–7.81(2H, m), 7.99–8.03(2H, m), 9.66(1H, s), 10.38(1H, s) |
| 28 | 3,4-(Me)₂—Ph | F+: | 483 |
| | | N1: | 1.97–2.20(4H, m), 2.24(6H, s), 2.67–2.76(1H, m), 2.96–3.30(4H, m), 4.37(2H, s), 7.17–7.27(3H, m), 7.79(2H, d), 8.00(2H, d), 9.66(1H, s), 10.36(1H, s) |

TABLE 8-continued

| | | | |
|---|---|---|---|
| 29 | 3,5-(Me)₂—Ph | F+: | 483 |
| | | N1: | 1.98–2.12(4H, m), 2.30(6H, s), 2.65–2.78(1H, m), 2.93–3.10(4H, m), 4.36(2H, s), 7.00–7.12(3H, m), 7.79(2H, d), 8.00(2H, d), 9.66(1H, s), 10.37(1H, s) |
| 30 | Me—[ring]—Me (with Me) | F−: | 495 |
| | | N1: | 1.83–2.52(4H+9H+1H, m), 2.99–3.26(4H, m), 4.18(2H×0.9, s), 4.48(2H×0.1, s), 6.88(2H×0.1, s), 7.01(2H×0.9, s), 7.74–7.82(2H, m), 7.94–8.03(2H, m), 9.66(1H, s), 10.36(1H, s) |
| 31 | Me—[ring]—Me (with F) | F−: | 499 |
| | | N1: | 1.82–2.44(6H+5H, m), 2.98–3.30(4H, m), 4.21(2H×0.85, s), 4.50(2H×0.15, s), 6.95(2H×0.15, d), 7.08(2H×0.85, d), 7.75–7.82(2H, m), 7.97–8.04(2H, m), 9.66(1H×0.85, s), 9.66(1H×0.15, s), 10.40(1H, brs) |
| 32 | [Me-Ph-Me-F ring] | F+: | 487 |
| | | N1: | 1.97–2.11(4H, m), 2.26(3H, brs), 2.63–2.74(1H, m), 2.95–3.07(4H, m), 4.38(2H, s), 7.21–7.45(3H, m), 7.79(2H, d), 8.00(2H, d), 9.66(1H, s), 10.39(1H, s) |
| 33 | [Me-indanyl ring] | F−: | 493 |
| | | N1: | 1.96–2.20(6H, m), 2.70–2.78(1H, m), 2.84–3.08(8H, m), 4.37(2H, s), 7.04–7.33(3H, m), 7.79(2H, d), 8.00(2H, d), 9.66(1H, s), 10.37(1H, s) |

TABLE 9

| | | | |
|---|---|---|---|
| 34 | 4-Me-3-Br—Ph | F−: | 546 |
| | | N1: | 1.96–2.16(4H, m), 2.38(3H, s), 2.66–2.77(1H, m), 2.96–3.08(4H, m), 4.39(2H, s), 7.40–7.49(2H, m), 7.73–7.82(3H, m), 8.00(2H, d), 9.66(1H, s), 10.41(1H, s) |
| 35 | 3-F-4-Me—Ph | F+: | 487 |
| | | N1: | 1.97–2.07 (4H, m), 2.26 (3H, s), 2.69–2.77 (1H, m), 2.99–3.03 (4H, m), 4.39 (2H, s), 7.22–7.28 (1H, m), 7.31–7.42 (2H, m), 7.80 (2H, d), 7.99 (2H, d), 9.66 (1H, s), 10.40 (1H, s) |
| 36 | 3-Cl-4-Me-Ph | F+: | 503 |
| | | N1: | 1.97–2.11 (4H, m), 2.36 (3H, s), 2.65–2.78 (1H, m), 2.97–3.08 (4H, m), 4.39 (2H, s), 7.39 (1H, dd), 7.45 (1H, d), 7.60 (1H, d), 7.80 (2H, d), 7.99 (2H, d), 9.65 (1H, s), 10.40 (1H, s) |
| 37 | 4-Cl-3-Me-Ph | F+: | 503 |
| | | N1: | 1.95–2.09 (4H, m), 2.36 (3H, s), 2.65–2.76 (1H, m), 2.95–3.07 (4H, m), 4.39 (2H, s), 7.36 (1H, dd), 7.48 (1H, d), 7.51 (1H, d), 7.80 (2H, d), 7.99 (2H, d), 9.66 (1H, s), 10.40 (1H, s) |
| 38 | 4-F-3,5-(Me)₂—Ph | F+: | 501 |
| | | N1: | 1.94–2.12(4H, m), 2.24(6H, s), 2.64–2.74(1H, m), 2.94–3.08(4H, m), 4.35(2H, s), 7.23(2H, d), 7.79(2H, d), 7.99(2H, d), 9.66(1H, s), 10.38(1H, s) |

TABLE 9-continued

| | | | |
|---|---|---|---|
| 39 | 3-F-2,4-(Me)₂—Ph | F+: | 501 |
| | | N1: | 1.84–2.34(4H+3H+3H, m), 2.48–2.55(1H, m), 2.85–3.22(4H, m), 3.98(1H×0.9, d), 4.30(1H×0.1, d), 4.65(1H×0.9, d), 4.81(1H×0.1, d), 7.22(1H, t), 7.27(1H, d), 7.78(2H, d), 7.98(2H, d), 9.66(1H, s), 10.37(1H×0.9, s), 10.51(1H×0.1, s) |
| 40 | 2-F-4-Me—Ph | F+: | 487 |
| | | N1: | 1.90–2.18(4H, m), 2.30(3H×0.1, s), 2.36(3H×0.9, s), 2.62–2.68(1H, m), 3.01–3.23(4H, m), 3.99(1H, d), 4.77(1H, d), 7.13(1H, d), 7.25(1H, d), 7.50(1H, dd), 7.77(2H, d), 7.99(2H, d), 9.66(1H, s), 10.40(1H×0.9, s), 10.45(1H×0.1, s) |

While the invention has been described in detail and with reference to specific embodiments thereof, it will be apparent to one skilled in the art that various changes and modifications can be made therein without departing from the scope thereof.

This application is based on Japanese patent application No. 2003-290850 filed Aug. 8, 2003, the entire contents thereof being hereby incorporated by reference.

What is claimed is:

1. N-{2-[(4-Substituted phenyl)amino]-2-oxoethyl}tetrahydro-2H-thiopyran-4-carboxamide compound represented by the following general formula (I),

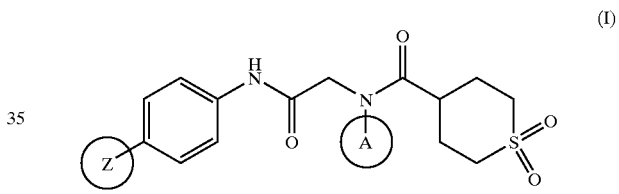

(I)

wherein the symbols in the formula have the following meanings;

Z: a 1,2,4-oxadiazol-3-yl or 4-oxazolyl group;

A: a phenyl group substituted with one methyl group, which may or may not have additional one or two substituents selected from the group consisting of a methyl group and halogen atoms, or a 5-indanyl group.

2. A compound according to claim 1, where Z is a 1,2,4-oxadiazol-3-yl group.

3. A compound according to claim 1, where Z is a 4-oxazolyl group.

4. A compound according to claim 1, where A is a phenyl group substituted with one methyl group, which may or may not have additional one or two substituents selected from the group consisting of a methyl group and halogen atoms.

5. A compound according to claim 1, where A is a 5-indanyl group.

6. A compound according to claim 1, which is selected from the group consisting of:

N-(2,6-dimethylphenyl)-N-(2-{([4-(1,3-oxazol-4-yl)phenyl]amino}-2-oxoethyl)tetrahydro-2H-thiopyran-4-carboxamide 1,1-dioxide, N-(4-methylphenyl)-N-(2-{[4-(1,3-oxazol-4-yl)phenyl]amino}-2-oxoethyl)tetrahydro-2H-thiopyran-4-carboxamide 1,1-dioxide, N-(3-methylphenyl)-N-(2-{[4-(1,3-oxazol-4-yl)phenyl]amino}-2-oxoethyl)tetrahydro-2H-thiopyran-4-carboxamide 1,1-dioxide, N-(2-methylphenyl)-N-(2-{[4-(1,3-oxazol-4-yl)phenyl]amino}-2-oxoethyl)tetrahydro-2H-thiopyran-4-carboxamide 1,1-dioxide, N-(2,4-dimethylphenyl)-N-(2-{[4-(1,3-oxazol-4-yl)phenyl]amino}-2-oxoethyl)tetrahydro-2H-thiopyran-4-carboxamide 1,1-dioxide, N-(3,4-dimethylphenyl)-N-(2-{[4-(1,3-oxazol-4-yl)phenyl]amino)-2-oxoethyl}tetrahydro-2H-thiopyran-4-carboxamide 1,1-dioxide, N-(2,3-dihydro-1H-inden-5-yl)-N-(2-{[4-(1,3-oxazol-4-yl)phenyl]amino}-2-oxoethyl)tetrahydro-2H-thiopyran-4-carboxamide 1,1-dioxide, N-(4-chloro-3-methylphenyl)-N-(2-{[4-(1,3-oxazol-4-yl)phenyl]amino}-2-oxoethyl)tetrahydro-2H-thiopyran-4-carboxamide 1,1-dioxide, N-(3-fluoro-4-methylphenyl)-N-(2-{[4-(1,3-oxazol-4-yl)phenyl]amino}-2-oxoethyl)tetrahydro-2H-thiopyran-4-carboxamide 1,1-dioxide, N-(3-fluoro-2,4-dimethylphenyl)-N-(2-{[4-(1,3-oxazol-4-yl)phenyl]amino}-2-oxoethyl)tetrahydro-2H-thiopyran-4-carboxamide 1,1-dioxide, N-(3,5-difluoro-4-methylphenyl)-N-(2-{[4-(1,3-oxazol-4-yl)phenyl]amino}-2-oxoethyl)tetrahydro-2H-thiopyran-4-carboxamide 1,1-dioxide, N-(2-fluoro-4-methylphenyl)-N-(2-{[4-(1,3-oxazol-4-yl)phenyl]amino}-2-oxoethyl)tetrahydro-2H-thiopyran-4-carboxamide 1,1-dioxide, N-(2,3-dimethylphenyl)-N-(2-{[4-(1,2,4-oxadiazol-3-yl)phenyl]amino}-2-oxoethyl)tetrahydro-2H-thiopyran-4-carboxamide 1,1-dioxide, N-(2,4-dimethylphenyl)-N-(2-{[4-(1,2,4-oxadiazol-3-yl)phenyl]amino}-2-oxoethyl)tetrahydro-2H-thiopyran-4-carboxamide 1,1-dioxide, N-(2,6-dimethylphenyl)-N-(2-{[4-(1,2,4-oxadiazol-3-yl)phenyl]amino}-2-oxoethyl)tetrahydro-2H-thiopyran-4-carboxamide 1,1-dioxide, N-(4-fluoro-2,6-dimethylphenyl)-N-(2-{[4-(1,2,4-oxadiazol-3-yl)phenyl]amino}-2-oxoethyl)tetrahydro-2H-thiopyran-4-carboxamide 1,1-dioxide, N-(2,3-dihydro-1H-inden-5-yl)-N-(2-{[4-(1,2,4-oxadiazol-3-yl)phenyl]amino}-2-oxoethyl)tetrahydro-2H-thiopyran-4-carboxamide 1,1-dioxide, N-(3-fluoro-4-methylphenyl)-N-(2-{[4-(1,2,4-oxadiazol-3-yl)phenyl]amino}-2-oxoethyl)tetrahydro-2H-thiopyran-4-carboxamide 1,1-dioxide, N-(4-chloro-3-methylphenyl)-N-(2-{[4-(1,2,4-oxadiazol-3-yl)phenyl]amino}-2-oxoethyl)tetrahydro-2H-thiopyran-4-carboxamide 1,1-dioxide, and N-(3-fluoro-2,4-dimethylphenyl)-N-(2-{[4-(1,2,4-oxadiazol-3-yl)phenyl]amino}-2-oxoethyl)tetrahydro-2H-thiopyran-4-carboxamide 1,1-dioxide.

7. A pharmaceutical composition comprising an N-}2-[(4-substituted phenyl)amino]-2-oxoethyl}tetrahydro-2H-thiopyran-4-carboxamide compound represented by the following general formula (I) and a pharmaceutically acceptable salt:

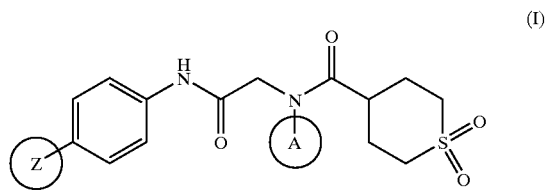

(I)

(the symbols in the formula have the following meanings;
Z: a 1,2,4-oxadiazol-3-yl or 4-oxazolyl group;
A: a phenyl group substituted with one methyl group, which may or may not have additional one or two substituents selected from the group consisting of a methyl group and halogen atoms, or a 5-indanyl group).

8. A pharmaceutical composition according to claim 7, which is an anti-herpesvirus agent.

9. A method for therapeutically treating diseases in which herpesvirus is involved, comprising administering an effective amount of an N-{2-[(4-substituted phenyl)amino]-2-oxoethyl}tetrahydro-2H-thiopyran-4-carboxamide compound represented by the following general formula (I),

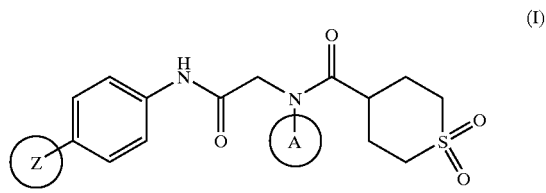

(I)

wherein the symbols in the formula have the following meanings;
Z: a 1,2,4-oxadiazol-3-yl or 4-oxazolyl group;
A: a phenyl group substituted with one methyl group, which may or may not have additional one or two substituents selected from the group consisting of a methyl group and halogen atoms, or a 5-indanyl group.

* * * * *